United States Patent [19]

Tepper

[11] Patent Number: 4,976,614
[45] Date of Patent: Dec. 11, 1990

[54] REMOVABLE ORTHODONTIC APPLIANCE

[76] Inventor: Harry W. Tepper, 535 Ocean Ave. #2B, Santa Monica, Calif. 90402

[21] Appl. No.: 221,132

[22] Filed: Jul. 19, 1988

Related U.S. Application Data

[63] Continuation-in-part of Ser. No. 11,728, Feb. 6, 1987, abandoned.

[51] Int. Cl.$^5$ .............................................. A61C 3/00
[52] U.S. Cl. ...................................... 433/18; 433/6; 433/20; 433/21
[58] Field of Search ..................... 433/6, 7, 9, 18, 20, 433/21, 22, 23, 24

[56] References Cited

U.S. PATENT DOCUMENTS

| | | | |
|---|---|---|---|
| 783,609 | 2/1905 | Canning | 433/21 |
| 1,139,170 | 5/1915 | Drissler | 433/21 |
| 1,142,467 | 6/1915 | Walker | 433/21 |
| 1,504,942 | 8/1924 | Comegys | 433/20 |
| 1,938,428 | 12/1933 | Johnson | 433/20 |
| 3,792,529 | 2/1974 | Goshgarian | 433/7 |
| 4,028,808 | 6/1977 | Schwartz | 433/7 |
| 4,037,324 | 7/1977 | Andreasen | 433/24 |
| 4,224,021 | 9/1980 | Foxman | 433/18 |
| 4,373,913 | 2/1983 | McAndrew | 433/23 |
| 4,424,031 | 1/1984 | Dahan | 433/18 |
| 4,433,956 | 2/1984 | Witzig | 433/7 |
| 4,468,196 | 8/1984 | Keller | 433/24 |

FOREIGN PATENT DOCUMENTS 568696  1/1933  Fed. Rep. of Germany ........ 433/20

OTHER PUBLICATIONS

"Orthodontics in General Dentist Practice", by Gordon G. Dickson, Pitman Medical Publishing Co., Ltd., London (1960).
The Orthodontist, vol. 2, No. 2, Autumn 1970.
Journal of Clinical Orthodontics, May 1972, vol. 6, No. 5, p. 284.
Journal of Clinical Orthodontics, Jul. 1972, vol. 6, No. 7, p. 386.
Journal of Clinical Orthodontics, Aug. 1972, vol. 6, No. 8, p. 461.
Journal of Clinical Orthodontics, Aug. 1974, vol. 8, No. 8, p. 462.
"Orthodontips", published by Ohlendorf Company, St. Louis, Mo., Jul. 1977.
"Quintessence of Dental Technology", Dec. 1978, vol. 2, p. 48.
"Orthodontics", No. 4, Report 311, Apr. 1981.

Primary Examiner—John J. Wilson
Attorney, Agent, or Firm—Merchant & Gould

[57] ABSTRACT

A removable orthodontic appliance is firmly seated on the teeth on each side at a midregion by clasps which provide a base for a label filament serving as a reference arch, and curved lingual spring filament which urges the teeth against the reference. The lingual filament provides a gentle but constant force over a substantial distance to cause repositioning of selected teeth without the need for frequent readjustments. The mountings for the filaments comprise open loops having filament receiving sleeves at each end by means of which the positions and angles of the filaments may be adjusted but the filaments may be coupled in solely by mechanical means. The lingual filament may comprise a memory alloy having a temperature transition below normal body temperature so that it may initially follow the irregular profile of the teeth and continue to exert pressure over a substantial distance as the teeth are repositioned. A retainer device may use synthetic resin filaments of transparent material to hold the teeth against relapse.

26 Claims, 7 Drawing Sheets

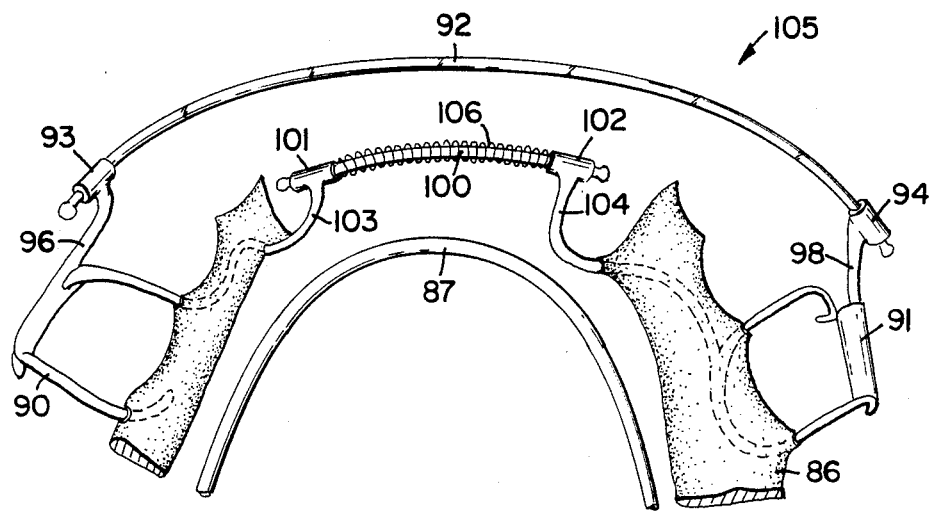

REMOVABLE ORTHODONTIC APPLIANCE

CROSS-REFERENCE TO RELATED APPLICATION

This is a continuation-in-part application of Ser. No. 011,728, filed Feb. 6, 1987, now abandoned by Harry William Tepper, for "REMOVABLE ORTHODONTIC APPLIANCE".

BACKGROUND OF THE INVENTION

There are two principal types of orthodontic appliances for straightening teeth or holding them in position after correction. Non-removable appliances are based on the use of wires coupled to elements cemented to the teeth and removable only by mechanical means. While this is an accepted and proven approach, the non-removable appliances require cumbersome and unsightly devices which are very inconvenient to the user and which must often be left in place for a long period of time. The other principal class is the removable appliance, one of which typically employs a pair of resilient arch wires, one for the labial side of the teeth, and the other for the lingual side. These wires are welded or soldered to a clasp or anchoring structure typically coupled to midregion teeth on each side and secured together across the roof of the mouth by an expansion plate or wire. By adjusting the length or curvatures of the labial and lingual arch wires, teeth can be urged toward the more ideal position. Although there are a substantial number of variations of this general class of orthodontic appliance, they all present particular difficulties in one or a number of specific respects. After repositioning displaced teeth a retaining appliance must be used for a substantial period of time because the teeth in 80% of the cases tend to relapse within various periods of time. If relapse has occurred the ordinary or usual retainer will not fit; therefore, retreatment with fixed appliances is necessary depending on the degree of relapse. Again the problem of unsightliness must be confronted.

For most treatments using resilient arch wires a succession of adjustments are needed as the teeth gradually are moved to the desired positions and orientations. This means that the wearer must repeatedly be examined, the adjustments made and tested, and then the appliance must be worn for a time, until a final adjustment is made for the last increment of repositioning. In one widely used prior art system lingual springs are used until a degree of repositioning is achieved, following which a high labial wire is used with descending pins at each tooth to control position. Using conventional arch wires of high spring force, problems typically arise from the amplitude or time-varying characteristic of the forces that are exerted. If the forces applied are too great, the root of a tooth can be pathologically loosened. If the force drops off substantially as positions change, a long time may be required to reach the final position for an adjustment. In comparison, removable orthodontic appliances typically have had to be used, with successive adjustments, over long periods of time, i.e. typically more than several years. The orthodontic corrections required can involve much more than movement of teeth in the posterior or anterior direction. Individual teeth may require rotation in a distal or mesial manner relative to a vertical or horizontal axis and this, of course, should be done concurrently with other repositioning. In other words, teeth may be moved in three planes of spaces to positions selected to occlude properly with teeth in opposing arches.

Appliances, whether removable or not, often interfere with both speaking and eating. Moreover, improperly placed or large bodies beneath the tongue tip are disruptive of the proprioceptive sense and represent a particular problem. The expansion plate used to bridge the palate is not only a large bulky appliance, but can introduce painful pressures if asymmetric forces are generated in the occlusal (biting) direction.

In very early work on correctional appliances a different approach was proposed by Drissler in U.S. Pat. No. 1,139,170. Drissler suggested primarily that anchoring structures on each side in the region of the back teeth could be interconnected by a pivotable arch wire, a proposal of questionable merit. He also suggested, however, that correction of front tooth position, both in the radial direction and to some extent rotationally, could be made by using spring wires not attached to the teeth. His proposed device used a labial spring wire and a pair of free-ended lingual spring wires, each anchored in a rearward position and extending forwardly to a separating gap. This device was not satisfactorily employed, as far as is known, and a number of obvious reasons present themselves. For example, the outward forces exerted along the length of the free-ended lingual wires vary with position. Also, the wires inevitably are displaced along the slanted tooth surfaces toward the tooth ends, thus diminishing or even eliminating completely the forces exerted. They probably also are displaced merely because of gravity. In addition, the Drissler structure interposes a mass of wires interfering with tongue action and produces blocking of normal contact with the rugae.

There is therefore a general need for a removable orthodontic appliance that is less obvious cosmetically, provides more uniform forces, requires less adjustment and introduces a minimum of interference into the functions of the tongue and teeth. In addition, there are needs for appliances which can be utilized not only in repositioning teeth and retaining tooth position after corrections have been made. The device should be readily adjustable to match the specific needs and conditions of the individual patient. Thereafter, however, it should be able to perform its function indefinitely without need for change, but should be adjustable if the need arises. Further, it is preferable to be able to prefabricate as much of the device as is feasible, to reduce costs and improve uniformity.

SUMMARY OF THE INVENTION

Removable orthodontic appliances and retainers when viewed from a frontal aspect in accordance with the invention employ confined spans of resilient filaments or metal wire anchored at each end in holders, which can be set in position and angle to seek to define a corrective arc forcing the teeth toward a reference arc. Light but constant forces exerted by a lingual filament or metal wire in contact with the teeth are sufficient to displace or retain the teeth against a labial filament in contact with the opposing side of the teeth. The holders are sleeves advantageously mounted on the ends of adjustment loops coupled to clasps fastened to a midregion between the anterior teeth and the last molars. Intercoupling arches between the clasps are configured for installation of appliances on upper or lower teeth. By using small sleeves as the end holders to closely receive the filaments or wires, filament or wire materials dissimilar from the sleeves can be inserted, set, and replaced without soldering or other heat treatment. The needed forces can then be applied by using transparent plastic filaments or memory wire such as nickel titanium or other metallic wire. The device presents on the lingual aspect a minimal interference with the proprioceptive sense because no structure is introduced under the tongue as in other removable appliances.

In one example of a corrective appliance, a gentle and substantially constant displacing force is applied on the lingual side by a temperature responsive memory spring filament formed as an arch and seated at each end within mating metal tubing sections. The memory wire, typically a nickel titanium alloy, is soft and deformable below a transition temperature range but becomes resilient or rigid and seeks to revert to a prior geometry when at a temperature above that range. The restoring forces of the memory metals are derived from the memory characteristic as well as compliance. Thus the lingual wire can provide substantially constant restoring forces on the teeth through significant distances. It is preferred to employ a lingual memory wire having a transition temperature between ambient room temperature and body temperature, because it may be impressed when soft at ambient temperature along the teeth to follow the irregular profile they present, and then provides a substantial length for expansion as the teeth move into position.

The end clasps for the labial and lingual wires are fastened around selected teeth on each side of the mouth, such as the upper second pre-molars or bicuspids, to give mechanical advantage. A uniquely arranged and functioning palatal arch interconnects the clasps in an appliance for the upper teeth. The palatal arch comprises a spring wire formed of a continuity of sinuous segments which mechanically bias the clasps outwardly to provide an expansion effect. The limits of the expansion are preset by limiting sleeves which encompass adjacent palatal wire lengths in the arch and prevent outward movement beyond the predetermined limit. With this arrangement, the palatal wire yields to differences in forces and displacements between opposite sides, and in the occlusal direction. Thus no discomfort arises because of differential force reactions in movements between the opposite sides.

A retainer in accordance with the invention advantageously uses synthetic filaments of sufficient gauge to have substantial compliance and freedom from stretch. These filaments additionally are transparent and therefore unobtrusive cosmetically. They are disposed in controlled span arcs mounted in sleeves at each end that may be adjusted in position and angle, so that the arcs of filaments exert gentle but constant anti-relapse forces against the flat surfaces of the teeth. Clasps coupled to teeth in the midregion provide anchor regions not only for the filaments and their holders but also for palatal wings of plastic resin, which are joined by arch wires above the tongue or across the palate. Preferably, the lingual filament is the core for a coil spring which exerts an outward force against the sleeves at each end, thus resisting relapse or adding a restoring force if some relapse has taken place. The structure may be compressed so it can be installed despite a relapse, and alternatively for this application the support structure can be expansible.

The lingual wires can be varied in different ways in accordance with the invention. In one example, a pair of lingual wires extending from opposite sides overlap each other on the posterior side of the teeth, and small buttons are glued to the teeth so that these free-ended wires may be snapped into position. In another example, similarly overlapped labial wires may include small terminal hooks, which can be joined by a dental elastic, so that the overlapping ends of the two wires are pulled toward each other, tending to increase the arch of the wire and exert more pressure on the adjacent teeth.

The labial arch wire can serve as the anchor for one end of an auxiliary length of memory wire secured at its other end to a button attached to the face of a tooth that must be rotated. Thus, dependent on the position and attitude of engagement, tangential or perpendicular forces can be applied to turn the tooth about a horizontal or vertical axis.

Separately, a button can be added to the labial surface of a tooth above or below the nominal path of the labial wire, as desired to cause intrusion or extrusion of that tooth. For intrusion, for example, the labial wire is positioned over the button, so as to tend to force the tooth downwardly a desired increment during installation of the appliance.

BRIEF DESCRIPTION OF THE DRAWINGS

A better understanding of the invention may be had by reference to the following description, taken in conjunction with the accompanying drawings, in which:

FIG. 11 is a fragmentary view of the retainer of FIG. 8, useful in explaining the manner in which adjustments may be made;

DETAILED DESCRIPTION OF THE INVENTION

Figure 1:
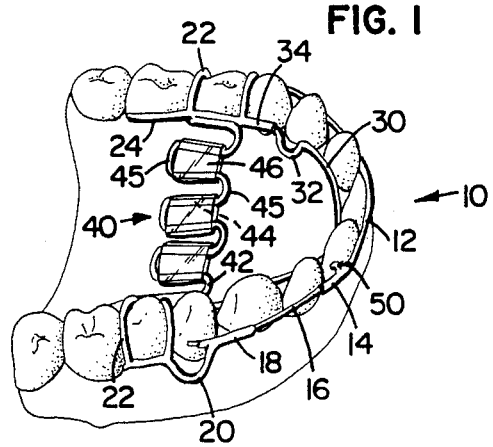
FIG. 1 is a perspective view of a removable orthodontic appliance in accordance with the invention for attachment to upper teeth, viewed in inverted position.

Referring now to FIGS. 1-6, an exemplification of the invention is shown as a removable orthodontic appliance 10, principally shown as used for the upper teeth, but also depicted (FIG. 3) as a separate appliance 10' configured for the lower teeth. The appliance 10 includes a thin labial wire 12, here of substantially rigid material of approximately 0.016" diameter, formed into an idealized curve or arch encompassing the anterior surfaces of at least the centrals, laterals and cuspids. The labial wire 12 is sealed at each opposite end in a small tubing section 14. The arrangements on both sides are alike, so that only one need be described in detail hereafter.

Each short tubing section, such as tube 14, receives a different end of the labial wire 12, which may be secured by soldering or other known means, such as by mechanical crimping of the tube 14. The tube 14 forms part of a prefabricated end structure having a short interconnecting wire segment 16 leading to a small base tube 18 to which a partially open side loop 20 (FIGS. 2 and 5) is joined. The side loop 20 is not closed so that it may be compressed or expanded in the anterior-posterior direction, adjusting the arch form. The posterior end of each side loop 20 is joined to a clasp 22 that is firmly seated in encircling relationship about a selected tooth, such as the second pre-molar or bicuspid, so that maximum leverage advantage may be obtained. To enhance the rigidity of this appliance 10 when once installed, a posterior lingual extension 24 bears against at least one molar on each side. This also serves to apply expansion force to move the upper first molars laterally.

A lingual wire 30 having a smaller radius of curvature than the labial wire 12 engages the posterior surfaces of the centrals, laterals and cuspids, and has an open loop 31, 32 of U shape adjacent each end. The ends are each in a different posteriorly directed tubing section 33, 34. The lingual wire 30 seeks to form an ideal arch geometry when above its transition temperature range. The lingual wire is a memory metal of nickel titanium alloy generally known as Nitinol and sold commercially under the trademark "Tinel" as a shape memory alloy by Raychem Corp. of Menlo Park, Calif.

This type of material has unique physical and temperature responsive properties, in that it has selectable transition temperature ranges dependent upon the contents of the alloy. Below the transition temperature range the metal is in its martensitic state, in which it is soft and can be deformed. Above the transition range the metal reverts to an austenitic state in which it regains strength and seeks to return to a predetermined shape, which can be a particular curve for the wire. The memory metal also can be greatly distorted without exceeding its yield point. A memory wire as used here can, for example, be tied in a knot without assuming a permanent set. Thus permanent distortion resulting from deformation during manufacture is not a problem. In returning to its memory shape a spring force is derived from the memory characteristic of the metal as well as the shape distortion. Consequently the spring forces exerted can be light but substantially uniform over a range, and do not vary substantially as the teeth change position toward the desired orientation. This application of a substantially uniform force throughout a wide excursion range is just what is needed for gently but relatively rapidly urging teeth into a selected position. A typical high spring material used for dental applications is different, in that it exerts a very high force when the adjustment is first made, but thereafter the force rapidly decreases as position changes.

Memory metals were earlier disclosed in U.S. Pat. No. 3,174,851 to Buehler et al and in U.S. Pat. No. 3,351,463 to Rozner et al. Applications of such metals are shown and described in the following patents:

| U.S. Pat. No. 3,285,470 | Frei et al |
|---|---|
| U.S. Pat. No. 3,391,882 | Johnson et al |
| U.S. Pat. No. 3,403,238 | Buehler et al |
| U.S. Pat. No. 3,416,342 | Goldstein et al |
| U.S. Pat. No. 3,740,839 | Otte et al |
| U.S. Pat. No. 3,861,030 | Otte et al |
| U.S. Pat. No. 4,022,519 | Hill |
| U.S. Pat. No. 4,379,575 | Martin |
| U.S. Pat. No. 4,619,568 | Carstensen |

The small tubing sections 33, 34 into which the lingual wire 30 is set are crimped to frictionally secure the lingual wire 30 at a given length without any heating effects on the wire 30. The loops 31, 32 near each end of the wire 30 present a stop which prevents further entry of the wire 30 ends into the associated tubing sections 33, 34. The tubing sections 33, 34 are also joined to the clasps 22 at each side. The posterior extensions 24 which engage at least one posterior molar can be soldered into the tubing sections 33, 34 or along the clasps 22 at each side.

The side tubings 33, 34 and clasps 22 also provide securement regions for each end of a sinuous or accordion folded palatal arch device 40 which is fitted to be substantially mated to the roof of the user's mouth. The palatal arch device 40 comprises a periodic structure formed by a wire 42 that is continuous in form but has cyclic variations defined by long sides 44 joined by transverse end segments 45. The adjacent long sides 44 are paired together in coextensive spaced apart segments to form a slightly diverging angle, and each pair is encompassed by a sleeve 46 formed of heat shrinkable plastic tubing. In prefabricating the palatal arch device 40, the wire 42 is given a sinuous or accordion-like configuration but is held at a given position as the heat shrinkable tubing is first attached and then heated to shrink the tubing into a tight fitting sleeve 46. This compresses the palatal arch device 40 to a desired extent suitable for fitting between the small tubing sections 33, 34 to which it is secured. In position between the anchoring clasps 22 the palatal arch device 40 fits snugly across the bridge of the mouth and acts to provide a gentle spreading force on the clasps 22. It can also be compressed somewhat during chewing and facial movements. However, the palatal arch device 40 cannot expand beyond a certain limit, determined by the preset transverse dimension of the sleeves 44 to bear against the palate.

Figure 6:
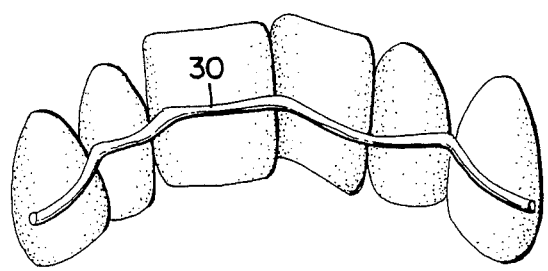
FIG. 6 is a fragmentary perspective view of a portion of the device of FIGS. 1-5, showing the initial conformation of the lingual wire to badly positioned teeth.

The preferred lingual wire 30 in this example is one which has a transition range between normal ambient room temperature (e.g. approximately 75° F.) and body temperature (e.g. approximately 98.6° F.). (It will be recognized that a somewhat lower limit can be used in practice if the wire is pre-cooled to a degree that is not uncomfortable or potentially harmful.) Below its transition temperature, the lingual wire 30 is soft and can be impressed against the surface of the teeth, following the profile presented, as seen in FIG. 6. The somewhat arbitrary or erratic path thus followed seeks to straighten when strength returns to the wire 30 at higher temperatures. Thus more material becomes available to urge the teeth toward the ideal curve as the teeth are displaced.

The appliance 10' for the lower teeth (FIG. 3) is like that described except that no palatal arch device 40 is used Instead the base of the tongue is ringed by an inner lingual arc wire 48 secured at each end to a different clasp 22.

Thus, still referring to FIGS. 1-6, it is seen that the desired properties for a removable orthodontic appliance are provided by this device. In order for the appliance 10 to be used, the orthodontist first selects the ideal curvature for the rigid labial wire 12, achieving fine adjustment as necessary with the expandable/contractible loops 20 joined to the clasps 22. The lingual wire 30 is preset to a given shape, typically a small ideal curvature, and joined to the tubing sections 33, 34 by crimping those sections with the chosen segment of lingual wire 30 exposed, the loops 31, 32 in the lingual wire 30 abutting the tubing section 33, 34 The palatal arch device 40 is, after fitting to the roof of the mouth, limited to its preset expansion by the sleeves 46. The lingual wire 30 constantly thrusts the teeth toward the labial reference wire 12 with a gentle pressure, typically of the order of approximately 2 ounces. As the teeth reposition, the memory wire 30 characteristic, the straightening effect on the bends in the wire, and the open end loops 31, 32 provide added length to insure that substantially constant force is applied so that no readjustment is needed. Thus, in a period of a relatively few months, the malformed teeth are repositioned into the reference location defined by the labial wire 12.

Typically, no adjustment is needed for the labial wire 12 or lingual wire 30 during this interval. If, however, an adjustment is needed it is effected simply by removing the appliance 10, then releasing and recrimping one or both of the tubing sections 33, 34 so as to lengthen the lingual wire 30. Alternatively or at the same time the end loops 31, 32 can be reformed or revised. Because the pressures are uniform and gentle, there is no danger of significant dislocation of the root or root resorption. The labial wire 12 may also be readjusted at the loops 20 to provide a new reference.

Concurrently, the flexible cross support provided by the palatal arch device 40 provides a supportive but suitably yielding transverse structure. The sleeves 46 which limit expansion of the spring segments defined by the long sides 44 and the transverse end segments 35 are substantially flush with the roof of the mouth on the upper side, but provide only smooth contact with and virtually no impediment or discomfort to the tongue. When a variation of forces or spaces between the teeth occurs in the occlusal direction, as when biting down on an object on one side, no painful reaction is felt. Heretofore, this has caused a sharp force or a substantial counterpressure to be exerted between the two sides because of prior art expansion plates. In the present example, however, the palatal arch device 40 yields to the distorting force, and no discomfort is felt.

Figure 2:
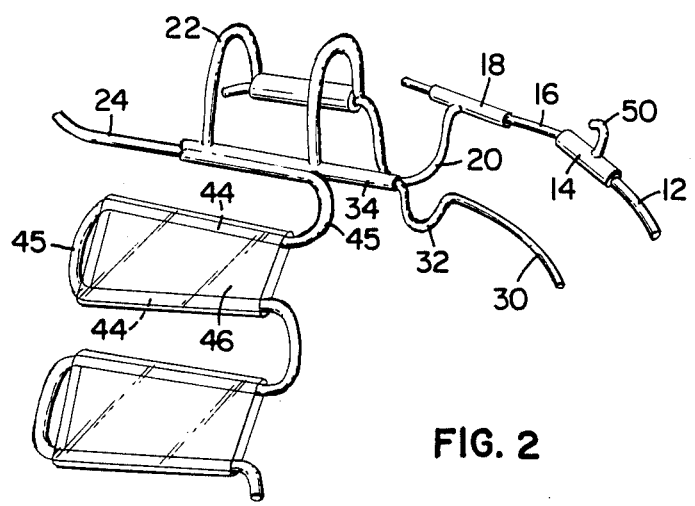
FIG. 2 is an enlarged fragmentary view of a portion of the appliance of FIG. 1 showing portions in greater detail and also viewed in inverted position.
Figure 3:
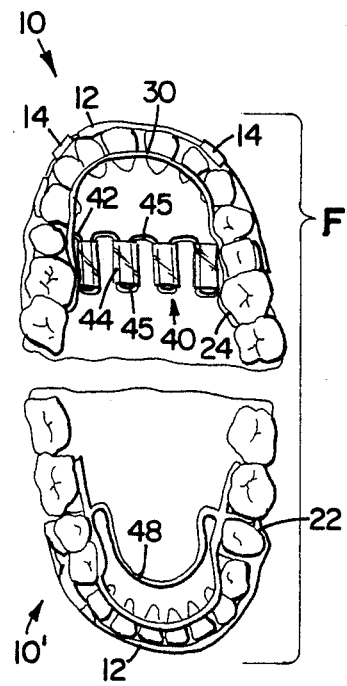
FIG. 3 is a plan view of a pair of the appliances as installed on both upper and lower teeth.
Figure 4:
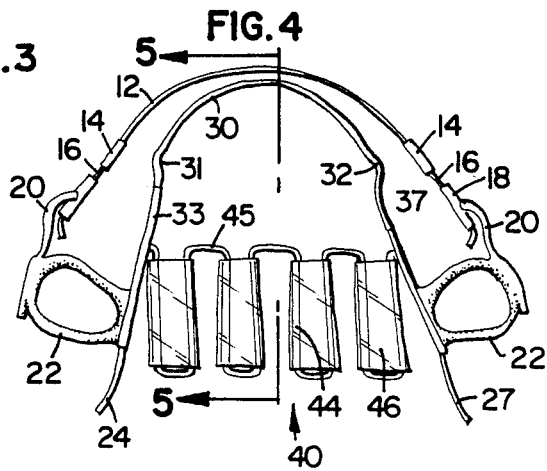
FIG. 4 is a top perspective view of the device of FIGS. 1 and 2.
Figure 5:
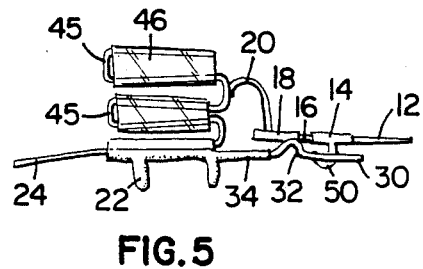
FIG. 5 is a side view of the device of FIG. 4, taken along the lines 5—5 in FIG. 4 and looking in the direction of the appended arrows.

As seen particularly in FIGS. 1, 2, and 5, the labial wire 12 may have attached a pair of hooks 50, joined to the tubes 4. Conventional stretchers (dental elastics, not shown) may be attached to the hooks 50, for the purpose of exerting greater pressures than heretofore described.

Figure 7:
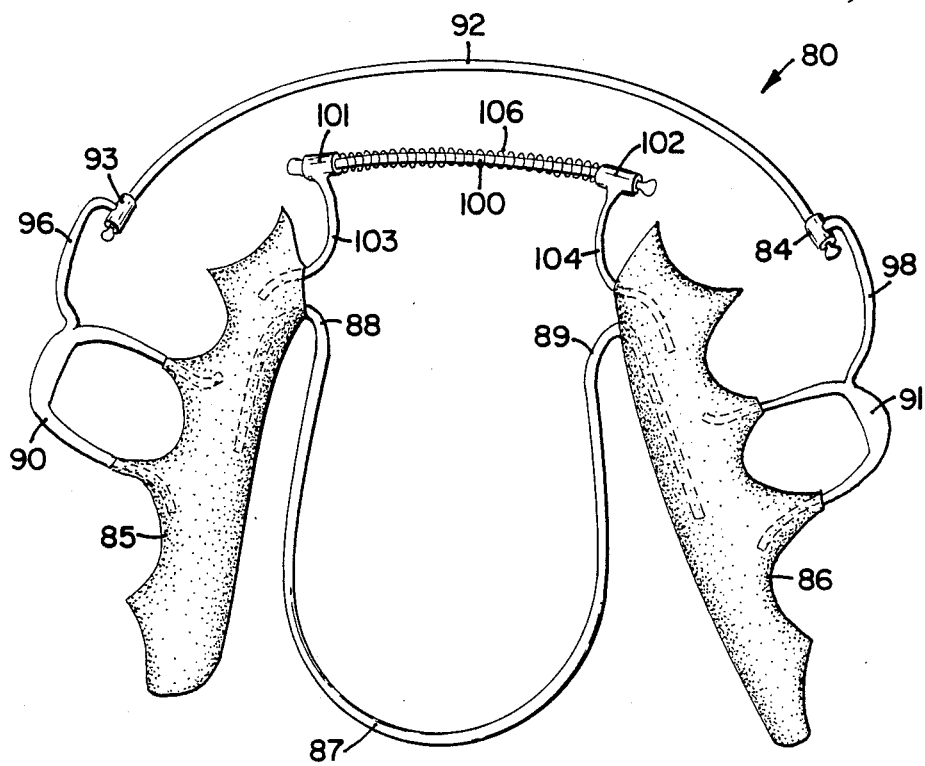
FIG. 7 is a top perspective view of a removable retainer system in accordance with the invention for the upper teeth.

As seen in FIG. 7 another device in accordance with the invention, depicted as used on an upper retainer 80, includes a pair of opposed facing palatal wings 85 and 86 which conform to and encompass the gingival region of a number of molars. Placed on either side of the mouth (upper palatal region as show in FIG. 7) the palatal wings 85,86 are coupled together by means of a palatal arch device 87 in the form of a curved wire whose distal ends 88 and 89 are embedded in respective ones of the wings. The arch device 87, which extends from the anterior portion of the palatal wings in a U shape and back across the roof of the mouth, is pre-stressed in compression thereby providing an outward force urging the wings 85,86 apart and pressing them against the gingival region with which they are in contact. The arch device 87 lies within the "valley" of the palate and does not interfere with the tongue.

A pair of clasps 90 and 91 whose contour conforms essentially to the outer surface of teeth (typically premolars) which they are to engage are also embedded in the palatal wings 85 and 86 respectively. The clasps 90 and 91 are located on opposite sides of the mouth and, in combination with the palatal wings, securely but removably mount the retainer 80 in place.

A labial filament 92 is supported between and secured to filament sleeves 93 and 94 slightly larger in internal diameter than the outer diameter of the filament 92. The sleeves 93 and 94 are spaced apart a predetermined distance so that a desired number of teeth are in contact with the labial filament 92 when the retainer is installed. The sleeve 93 is mounted on the end of a U-shaped wire loop 96 that is stiff but bendable and which in turn is coupled to the anterior side of clasp 90. Similarly the sleeve 94 is mounted on the end of another U-shaped stiff wire loop 98 that is coupled to the anterior side of clasp 91. The labial filament 92 is formed of transparent Nylon, preferably within the range from about 0.028" to 0.032∆ in diameter.

The labial filament 92 is thus suspended between sleeves 93 and 94 to define a reference arch against which teeth can be urged so as to be retained in the repositioned orientation. Typically the labial filament 92 functions essentially as a resilient spring to exert less than an ounce of reactive force against the teeth with which it is in contact, when the teeth are urged outwardly by forces from the lingual side. Alternatively the loops 96, 98 can be adjusted so as to place tension on the labial filament 92 as it engages adjacent teeth.

Acting in cooperation with the labial filament 92 is a lingual filament 100 which is positioned in the retainer 80 to provide a forcing arch against the posterior side of a desired number of teeth to prevent relapse.

Specifically the lingual filament 100 is suspended between and secured to hollow sleeves 101 and 102. The sleeves 101 and 102 are spaced apart by an adjustable distance, and settable at chosen angles, on U-shaped bendable wire loops 103, 104 anchored in the palatal wings 85, 86 respectively. The span of the lingual filament 100 is thus arranged so that a desired number of teeth come in contact, with the lingual filament 100 when the retainer is installed. The vertical position of the lingual filament 100 along the teeth, and the radius of the arc formed by the filament, as well as the initial vector angle, may be selected with this three dimensional capability. Advantageously, the lingual filament 100 is encompassed by a light coil spring 106 which extends between the sleeves 101, 102, in the arc defined by the lingual filament 100. The coil spring 106 is under compression between the sleeves 101, 102 so that it acts to provide both axial force outward on the sleeves and light radial force against the teeth.

Figure 8:
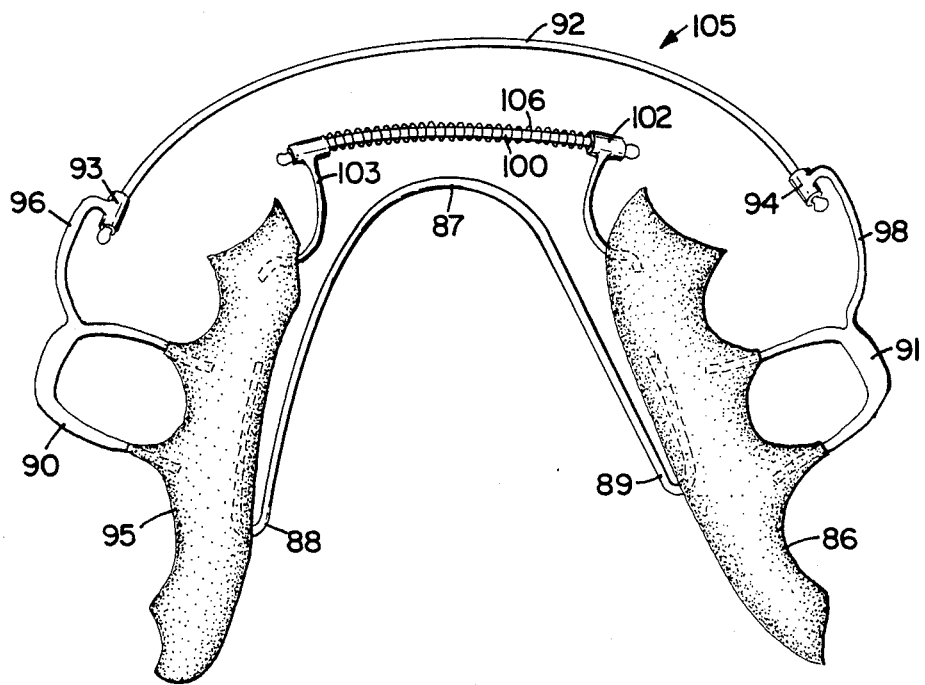
FIG. 8 is perspective view of a removable retainer in accordance with the invention for the lower teeth.

The basic configuration of the above described retainer 80 for the upper teeth is readily modified for prevention of lower teeth relapse to form a lower retainer 105 by revising the shape of the spring arch 106 to that which is shown in FIG. 8. In this Figure the lower retainer 105 has all parts which are essentially the same as were in FIG. 7 numbered in like fashion. The spring arch 106 extends forwardly from posterior anchored ends, so that it lies along an area in the vicinity of the base of the teeth and does not interfere with the tongue, or block off the rugae.

Figure 9:
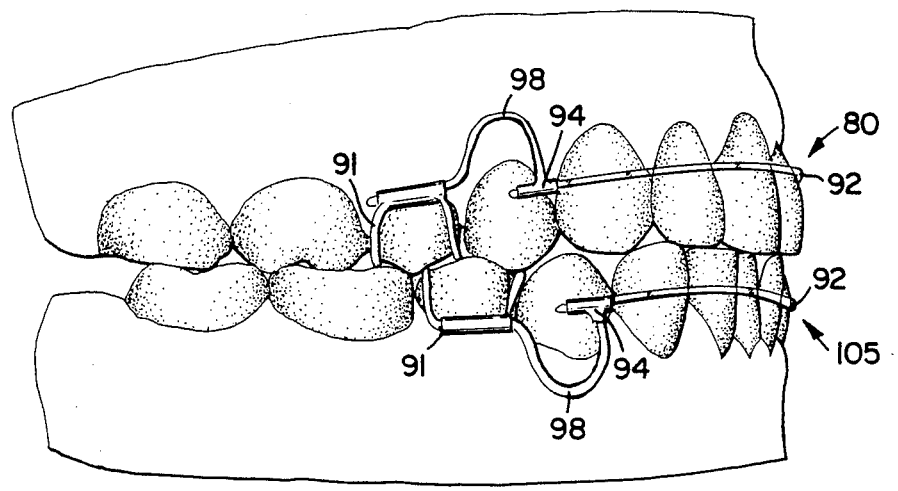
FIG. 9 is a side view of the arrangements of FIGS. 7 and 8, showing removable retainers installed on the upper and lower teeth of a patient.

With reference to FIG. 9, the upper and lower retainers 80, 105 are shown as installed to prevent relapse after correction of both upper and lower teeth sets. Prior to and during initial installation, as best seen in the enlarged view of FIG. 11, the sleeves 93, 94 and 101, 102 may be the sleeves set to vary both the height and radii of the arches formed by the filaments 92 and 100 respectively in accordance with the patient's needs. The stiff wire loops 96, 98, 103, 104 may be bent slightly rearwardly, forwardly, upwardly, and downwardly by standard tools used in the dental arts. Thus any one of a substantial number of repositionings of the filaments 92, 100 can be achieved with relative ease and speed to readily adapt the retainer 80, 105 to the minute corrections which may be required during the relapse prevention interval. The position of and the force exerted by the filament, 92, 100 on the teeth can thus be adjusted for maximum relapse prevention effect.

The labial and lingual filaments 92 and 100 are held in their respective end sleeves typically by crimping the filaments adjacent the anterior sides of the sleeve and heat distortion adjacent to posterior sides of the sleeves. When heated locally, as by a small flame, the filament end forms a bulb which provides secure retention.

Additional slight variations in the length of the filaments can be achieved by tensioning the filament and reducing the arc before heat deformation of the ends, thereby reducing the overall length of the filament. The use of Nylon filament material facilitates the above described procedure. Since the inside diameters of the sleeves preferably are sized to provide a close fit with the filament the filament may be retained against movement merely by distortion, as by pinching.

Figure 10:
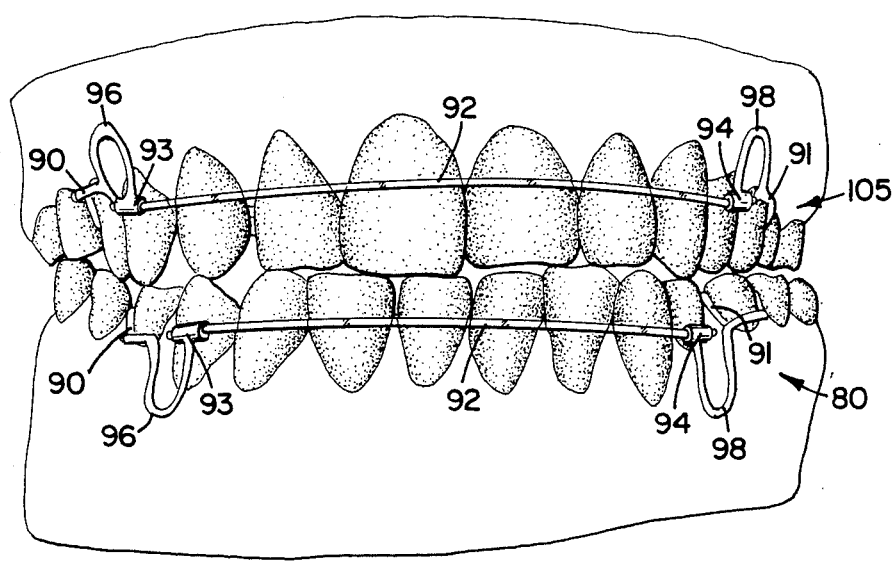
FIG. 10 is an enlarged front view of a portion of the installation of FIG. 9, showing the degree of unobtrusiveness achieved.

The lingual filaments 100 seen head on as in FIG. 10, are sufficiently small and transparent as to be unobtrusive in appearance. Also, the loops 96, 98 and 103, 104 are close to the gum line at each side of the mouth, so they are not readily visible in most persons.

It will be appreciated that relapse tendencies are counteracted throughout the teeth because the palatal wings span the molars and premolars while centrals, laterals and cuspids teeth are spanned by the filaments, and all elements exert light but constant outward forces as needed.

Figure 12:
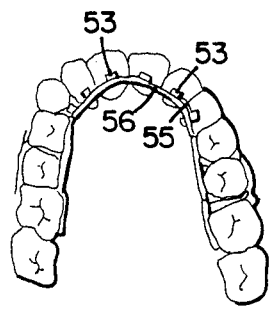
FIG. 12 is a fragmentary plan view of one alternate arrangement using free ended lingual wires, viewed from the underside relative to the upper teeth.
Figure 13:
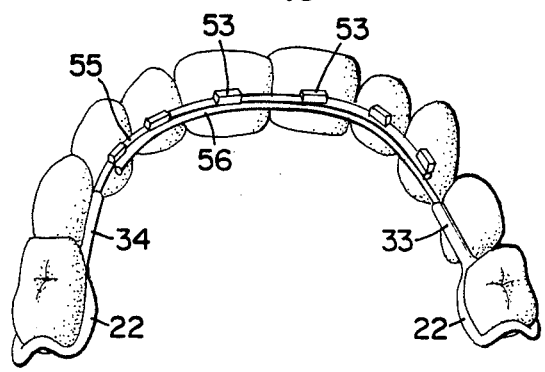
FIG. 13 is an enlarged fragmentary perspective view of the arrangement of FIG. 12, viewed in the same manner.

As seen in FIGS. 12 and 13 another variation in accordance with the invention disposes small buttons 53 on the posterior surfaces of a least a number of teeth in the central correction region. Each of a pair of overlapping lingual wires 55, 56 is then anchored only at one end in the appropriate end tubing 33 or 34, but may be moved into position by the use, who snaps the wires 55, 56 under the buttons 53. Both wires 55, 56 exert outward force on the teeth. This arrangement is particularly useful in making it more convenient for the individual user to remove and replace the appliance.

Figure 14:
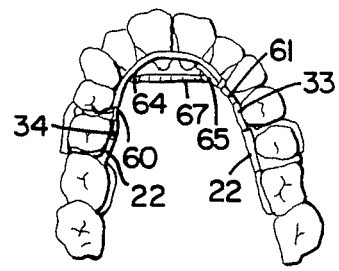
FIG. 14 is a plan view of another alternative arrangement in accordance with the invention using dental elastic and viewed form the underside relative to the upper teeth.
Figure 15:
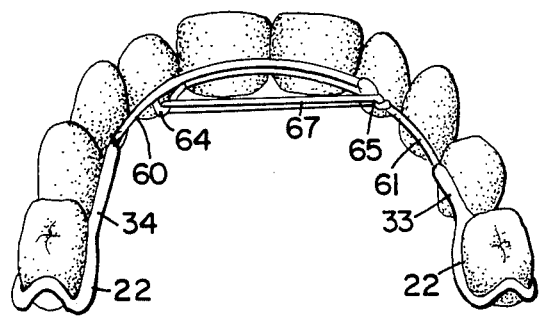
FIG. 15 is an enlarged fragmentary perspective view of the arrangement of FIG. 14, viewed in the same manner.

In accordance with another feature of the invention, referring now to FIG. 14 and 15, the lingual wire arrangement comprises a pair of free-ended lengths of memory wire 60, 61, each anchored in a different one of the end tubing sections 33, 34. The two wires 60, 61 overlap each other across the posterior portion of the centrals and laterals. Hooks 64, 65 are each anchored, as by crimping, to a different one of the lingual wires 60, 61 and are joined together by a dental elastic 67 which thus spans the overlap region. In trying to pull the ends of the wires 60, 61 together, the elastic 67 adds spring force onto the wires, seeking to urge them to a greater radius of curvature. Thus forces seeking to reposition teeth toward their desired locations are augmented. This technique can be used both to vary the force applied at different times and to achieve higher localized forces for individual areas.

Figure 16:
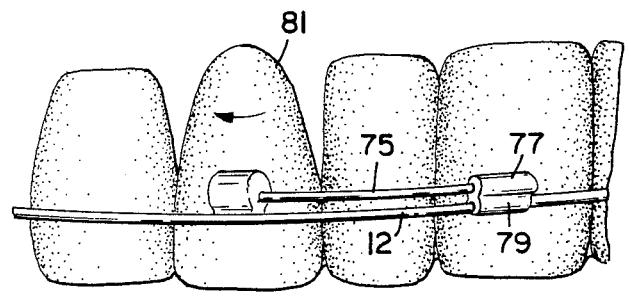
FIG. 16 is an enlarged fragmentary perspective view of another device in accordance with the invention, using an auxiliary memory wire to rotate tooth position.

As seen in FIG. 16, a short memory wire length 75 can be attached to the labial wire 12 to serve as a lever to provide a force that bears against an individual tooth at a region and in a direction needed for correction of an improper rotational or pivot position. Here the short memory wire 75 is anchored at one end by crimping in a sleeve 77 attached by solder 79 to the labial wire 12. At the tooth, a plastic button 81 is adhesively secured to the labial face at a desired position. The short memory wire 75 is positioned to be under longitudinal compression and to be substantially tangential to the tooth. Thus it exerts a rotational distal force about a vertical axis, turning the tooth back toward the desired position. It will be recognized that by changing the button 81 position and the angle of entry of the short memory wire 75 the tooth can be pivoted or rotated by distal or mesial forces in almost any sense desired. Although memory wire is generally preferred it will be recognized that other resilient wires may alternatively be used.

Although a number of different forms and expedients in accordance with the invention have been described above and shown in the drawings, it will be appreciated that the invention is not limited thereto but encompasses all variations and modifications in accordance with the appended claims.

What is claimed is:

1. A removable orthodontic appliance comprising:
    a labial arch wire registrable about anterior teeth surfaces to define a limit position, the labial arch wire being of rigid material;
    a pair of clasps removably engageable to midregion teeth on opposite sides of the mouth and secured to the labial arch wire at each end thereof;
    lingual arch wire means of spring material including means secured at each end to the clasps; and
    a transverse palatal wire arch structure coupled between the clasps and defining a bridge, the palatal arch structure being flexible in the occlusal direction and having limited expansibility, and the palatal arch structure further comprising a flexible wire having a sinuous configuration and means coupled thereto for limiting the relative expansion of the portions of the wire in the transverse direction.

2. The invention as set forth in claim 1 above, wherein the palatal arch wire has periodic, substantially rectangular segments and the means for limiting transverse expansion comprises plastic sleeves encompassing portions of the periodic segments.

3. The invention as set forth in claim 1 above, wherein the lingual arch wire comprises a temperature sensitive memory alloy, and wherein the means secured at each end comprises tube means secured at one end to the respective clasps and at the other end receiving the labial arch wire end and secured thereto.

4. The invention as set forth in claim 1 above, wherein the labial arch wire includes side loops adjacent the clasps, the side loops being open for changing the position of the labial arch wire in the anterior-posterior direction, and wherein the appliance further includes a posterior extension extending from the clasp and engageable to least one posterior tooth on each side.

5. The invention as set forth in claim 4 above, wherein the clasps are mountable on a midregion bicuspid to provide a maximum of leverage advantage.

6. The invention as set forth in claim 1 above, wherein the lingual arch wire means comprises at least one arch wire having one free end, and wherein the appliance further includes buttons mountable on the lingual surface of at least a number of teeth, whereby the lingual arch wire means may be snapped under the buttons to be retained in position in removable fashion.

7. The invention as set forth in claim 6 above, wherein the lingual arch wire means comprises a pair of wires each anchored at a different end and overlapping at the region of at least the centrals and laterals.

8. The invention as set forth in claim 7 above, wherein the appliance further includes plastic buttons on labial surfaces of the anterior teeth, to engage the labial wire above or below to intrude or extrude such teeth.

9. The invention as set forth in claim 1 above, wherein the lingual arch wire means comprises a pair of free-ended memory metal wires extending from the different ones of the clasps and overlapping adjacent their free ends, and wherein the lingual wires each include hooks adjacent their free ends and wherein the appliance further comprises resilient band means intercoupling the hooks to tend to increase the degree of arch of the arch wires.

10. The invention as set forth in claim 1 above, further including lever means including resilient wire bondable at one end to the labial surface of an anterior tooth and bondable at the other end to the labial wire to rotate the tooth about a desired axis.

11. The invention as set forth in claim 10 above, wherein the lever means includes button means that may be coupled to a chosen portion of the labial surface of a tooth and one end of the wire, and means for engaging the other end of the wire to the labial wire, and wherein the wire comprises a memory alloy.

12. A removable orthodontic appliance comprising:
a pair of wires, one of said wires comprising a rigid material that may be disposed anterior to the centrals, laterals and cuspids and the other of said wires comprising a spring wire that may be disposed posterior to the same teeth;
a pair of clasp means for securement to individual cuspids on each side of the teeth;
two pairs of sleeve members, the sleeve members of each pair being on opposite sides of the teeth and each pair being secured to a different clasp means and receiving the associated ends of a different one of the wires in the buccal region;
palatal arch means secured between the anchor means and conforming to the palate profile therebetween, the palatal arch means comprising a sinuous spring wire; and
means for restricting expansion of the palatal arch wire.

13. The invention as set forth in claim 12 above, wherein the sinuous spring wire comprises adjacent approximately parallel lengths joined by transverse end segments and the means for restricting expansion comprises heat shrunk sleeves encompassing the parallel lengths.

14. The invention as set forth in claim 13 above, wherein the rigid material wire defines a selected arch form, and wherein the spring wire has a temperature responsive memory characteristic.

15. The invention as set forth in claim 14 above, wherein the spring memory wire has a temperature transition range below normal body temperature and wherein the wire also includes an open loop near each end.

16. A removable retainer for preventing relapse of teeth that have been repositioned, comprising:
a pair of clasps, each securable on a similarly placed tooth on an opposite side of the mount;
a pair of molded palatal wings, each attached to a different one of the clasps and conforming to a surface area encompassing the gingival region of a number of pre-molars and molars and pressing thereagainst;
spring arch means embedded at each end in a different one of the palatal wings and coupling the palatal wings without interference with the tongue, the arch means providing an outward force on the palatal wings;
a pair of labial filament support members, each coupled to the labial anterior side of a different clasp and each including a U-shaped stiff wire loop and a terminal labial filament sleeve element connected thereto at the anterior end;
a pair of lingual filament support members, each coupled at a posterior end to a different one of the palatal wings, and each including a U-shaped stiff wire loop and a terminal lingual filament sleeve element connected thereto at the anterior end;
the labial filament sleeve elements being spaced apart by a first predetermined distance encompassing a number of front teeth;
a transparent nylon lingual filament of resilient character and between 0.028" and 0.032" in diameter coupled at opposite ends within the different lingual sleeve elements to form a forcing arch; and
a transparent nylon labial filament member of between 0.028" and 0.032" in diameter coupled at opposite ends within the different labial sleeve elements to form a reference arch, wherein the lingual filament sleeve elements and the lingual filament are positionable in the midregion of the height of the teeth along the first predetermined distance such that the filament is adapted to stay in the same vertical forcing arch position.

17. The retainer as set forth in claim 16 above, wherein the labial filament acts as a resilient spring adapted to exert less than of an ounce of force against the front teeth when engaged, and wherein the retainer further includes a coil spring encompassing the lingual filament and disposed under compression between the sleeve elements at each end thereof.

18. The retainer as set forth in claim 16 above, wherein the retainer is for the lower teeth and the arch wire defines an arch extending when mounted from the posterior region of the palatal wings under the tongue anterior region without blocking off the rugae.

19. The retainer as set forth in claim 16 above, wherein the retainer is for the upper teeth and the arch wire extending when mounted from the anterior portion of the palatal wings in a U shape back across the roof of the mouth.

20. The retainer as set forth in claim 16 above, wherein the palatal wings and labial filament are adapted to exert inward force when mounted throughout the tooth structure to prevent relapse.

21. The retainer as set forth in claim 20 above, wherein the stiff wire and loops and sleeve elements are adjustable in position and angle such that the radii and height of the arches may be varied, and the sleeve elements closely fit the filaments therewithin such that the filaments may be retained against movement merely by distortion.

22. The retainer as set forth in claim 21 above, wherein the labial and lingual filaments are nylon filaments mounted in the sleeve members by crimping adjacent the anterior sides and heat distortion adjacent the posterior sides.

23. In a removable orthodontic appliance for positioning or retaining a span of teeth, the combination comprising:
   a. means defining an arch filament, wherein the filament spans and is registrable with the surfaces of adjacent teeth;
   b. sleeve holder means mounted at each end of the arch filament means registrable adjacent teeth surfaces, wherein the arch filament means is coupled to the sleeve holder means at each end and is not substantially axially movable, whereby force is exertable when mounted on the teeth within the span;
   c. a coil spring wound about the arch filament and under compression between the sleeve holder means, and wherein the arch filament and spring are disposed when mounted on the lingual side and adapted to exert a radial force against the teeth;
   d. separate anchoring means adapted to couple to the midregion of the teeth when mounted at each side to the sleeve holder means at that side;
   e. means comprising adjustable wire loops coupling the separate anchoring means to the sleeve holder means at each side for retaining the sleeves in position at selectable spacings and angles, and wherein the arch filament means is coupled to the sleeve holder means by distortion of the filament on each side of the sleeve holder means; and
   f. labial arch filament means coupled to the separate anchoring means at each end and spanning and adapted to register with the surfaces of adjacent teeth.

24. The combination as set forth in claim 23 above, wherein the labial arch filament means is a substantially non-extensible, substantially transparent material, the arch filament defining a limiting, reference position.

25. The combination as set forth in claim 23 above, wherein the labial arch filament means is substantially a memory metal wire.

26. In a removable orthodontic appliance for positioning or retaining a span of teeth, the combination comprising:
   a. labial arch filament means registrable adjacent anterior teeth surfaces to define a limiting, reference position, the labial arch filament means being of a substantially inextensible material;
   b. lingual arch filament means of spring material, the lingual arch filament means when mounted spanning and being registrable adjacent posterior teeth surfaces;
   c. coil spring means encompassing the lingual arch filament means between the sleeve holder means, the coil spring being under compression, the spring producing an axial force outward on the sleeve means and acting to urge the labial arch filament means toward the teeth;
   d. sleeve holder means mounted at each end of the filament span on the lingual side registrable adjacent posterior teeth surfaces, the sleeve holder means comprising sleeves having internal diameters which provide a close fit with the filament means, wherein the lingual arch filament means is coupled to the sleeve holder means at each end and is not substantially axially movable relative thereto;
   e. separate anchoring means adapted to couple the midregion of the teeth when mounted at each side to the sleeve holder means at that side; and
   f. adjustable loops coupled at one end to the sleeve holder means, the loops being coupled at a second end to the anchoring means and being settable at selected angles and positions to vary the height, radius of curvature, and force exerted by the lingual arch filament.

* * * * *

UNITED STATES PATENT AND TRADEMARK OFFICE
CERTIFICATE OF CORRECTION

PATENT NO. : 4,976,614

DATED : December 11, 1990

INVENTOR(S) : Harry W. Tepper

It is certified that error appears in the above-identified patent and that said Letters Patent is hereby corrected as shown below:

In the Abstract, line 3, after "a" (second occurrence), "label" should read --labial--. Column 4, line 66, after "using" and before "dental" insert --a--; line 67, after "viewed" and before "the" (first occurrence), "form" should read --from--. Column 7, line 13, after "used" and before "Instead" insert a period (--.--); line 27, after "34" and before "The" insert a period (--.--). Column 8, line 1, after "tubes" and before the period (".") "4" should read --14--; line 42, before "in", "0.032Δ" should read --0.032''--. Column 9, line 65, after "of" and before "least", "a" should read --at--. Column 10, line 1, after "the" and before the comma (","), "use" should read --user--. Column 11, line 48, after "and" and before "at", "bondable" should read --bonded--. Column 12, line 25, after "the" and before the semicolon (";"), "mount" should read --mouth--.

Signed and Sealed this

Thirteenth Day of October, 1992

Attest:

DOUGLAS B. COMER

Attesting Officer

Acting Commissioner of Patents and Trademarks